US012714378B2

(12) United States Patent
Beck et al.

(10) Patent No.: US 12,714,378 B2
(45) Date of Patent: Aug. 25, 2026

(54) COMPATIBILITY PRODUCTION OF A PATIENT TABLE AND A MEDICAL IMAGING SYSTEM

(71) Applicant: Siemens Healthineers AG, Forchheim (DE)

(72) Inventors: Thomas Beck, Dormitz (DE); Christian Hetz, Pretzfeld (DE)

(73) Assignee: Siemens Healthineers AG, Forchheim (DE)

(*) Notice: Subject to any disclaimer, the term of this patent is extended or adjusted under 35 U.S.C. 154(b) by 0 days.

(21) Appl. No.: 18/740,885

(22) Filed: Jun. 12, 2024

(65) Prior Publication Data

US 2024/0420839 A1 Dec. 19, 2024

(30) Foreign Application Priority Data

Jun. 13, 2023 (DE) ..................... 10 2023 205 501.5

(51) Int. Cl.

| | |
|---|---|
| ***A61B 5/055*** | (2006.01) |
| ***A61B 5/00*** | (2006.01) |
| ***A61B 6/04*** | (2006.01) |
| ***A61B 6/10*** | (2006.01) |
| *G05B 19/4061* | (2006.01) |

(52) U.S. Cl.

CPC .............. *A61B 6/102* (2013.01); *A61B 5/055* (2013.01); *A61B 5/70* (2013.01); *A61B 5/704* (2013.01);

(Continued)

(58) Field of Classification Search

CPC ........... A61B 5/055; A61B 5/70; A61B 5/704; A61B 6/102; A61B 6/0407; A61B 6/0487;

(Continued)

(56) References Cited

U.S. PATENT DOCUMENTS 9,782,107 B1 * 10/2017 Greenhalgh ......... A61B 5/0037
2005/0264286 A1 * 12/2005 Harder ............... G01R 33/3415 324/309

(Continued)

FOREIGN PATENT DOCUMENTS

DE 102015211036 A1 12/2016
DE 202022102238 U1 5/2022

(Continued)

*Primary Examiner* — Keith M Raymond
*Assistant Examiner* — Johnathan Maynard
(74) *Attorney, Agent, or Firm* — Banner & Witcoff, Ltd.

(57) ABSTRACT

A computer-implemented method for producing compatibility of a patient table and of a medical imaging system. The patient table is designed to mount a patient during an examination with the medical imaging system. The method includes receiving a functional scope of the patient table, wherein the functional scope of the patient table (15) includes at least one function; receiving a functional scope of the medical imaging system, wherein the functional scope of the medical imaging system includes at least one function; comparing the functional scope of the patient table with the functional scope of the medical imaging system; and if at least one function is included only in the functional scope of the patient table and/or only in the functional scope of the medical imaging system, locking the at least one function.

14 Claims, 3 Drawing Sheets

(52) U.S. Cl.
CPC .......... *A61B 6/0407* (2013.01); *A61B 6/0487* (2020.08); *A61B 6/04* (2013.01); *A61B 6/10* (2013.01); *G05B 19/4061* (2013.01); *G05B 2219/45169* (2013.01); *G05B 2219/49143* (2013.01); *G05B 2219/49144* (2013.01); *G06T 2210/21* (2013.01)

(58) Field of Classification Search
CPC ........ A61B 6/04; A61B 6/10; G05B 19/4061; G05B 2219/45169; G05B 2219/49143; G05B 2219/49144; G06T 2210/21
See application file for complete search history.

(56) References Cited

U.S. PATENT DOCUMENTS

| | | | | |
|---|---|---|---|---|
| 2007/0016003 | A1* | 1/2007 | Piron | A61B 5/415 600/415 |
| 2008/0306377 | A1* | 12/2008 | Piron | A61B 8/5238 324/318 |
| 2015/0199487 | A1 | 7/2015 | Grauds et al. | |
| 2016/0139218 | A1* | 5/2016 | Possanzini | G01R 33/30 324/321 |
| 2016/0371442 | A1 | 12/2016 | Haeuser | |
| 2020/0143935 | A1 | 5/2020 | Feiweier et al. | |
| 2020/0390406 | A1* | 12/2020 | Xu | A61B 6/0407 |
| 2021/0393218 | A1* | 12/2021 | Jaber | A61B 6/08 |
| 2026/0007366 | A1* | 1/2026 | Leussler | A61B 5/704 |

FOREIGN PATENT DOCUMENTS

| | | | |
|---|---|---|---|
| EP | 3651161 | A1 | 5/2020 |
| EP | 4280221 | A1 | 11/2023 |

* cited by examiner

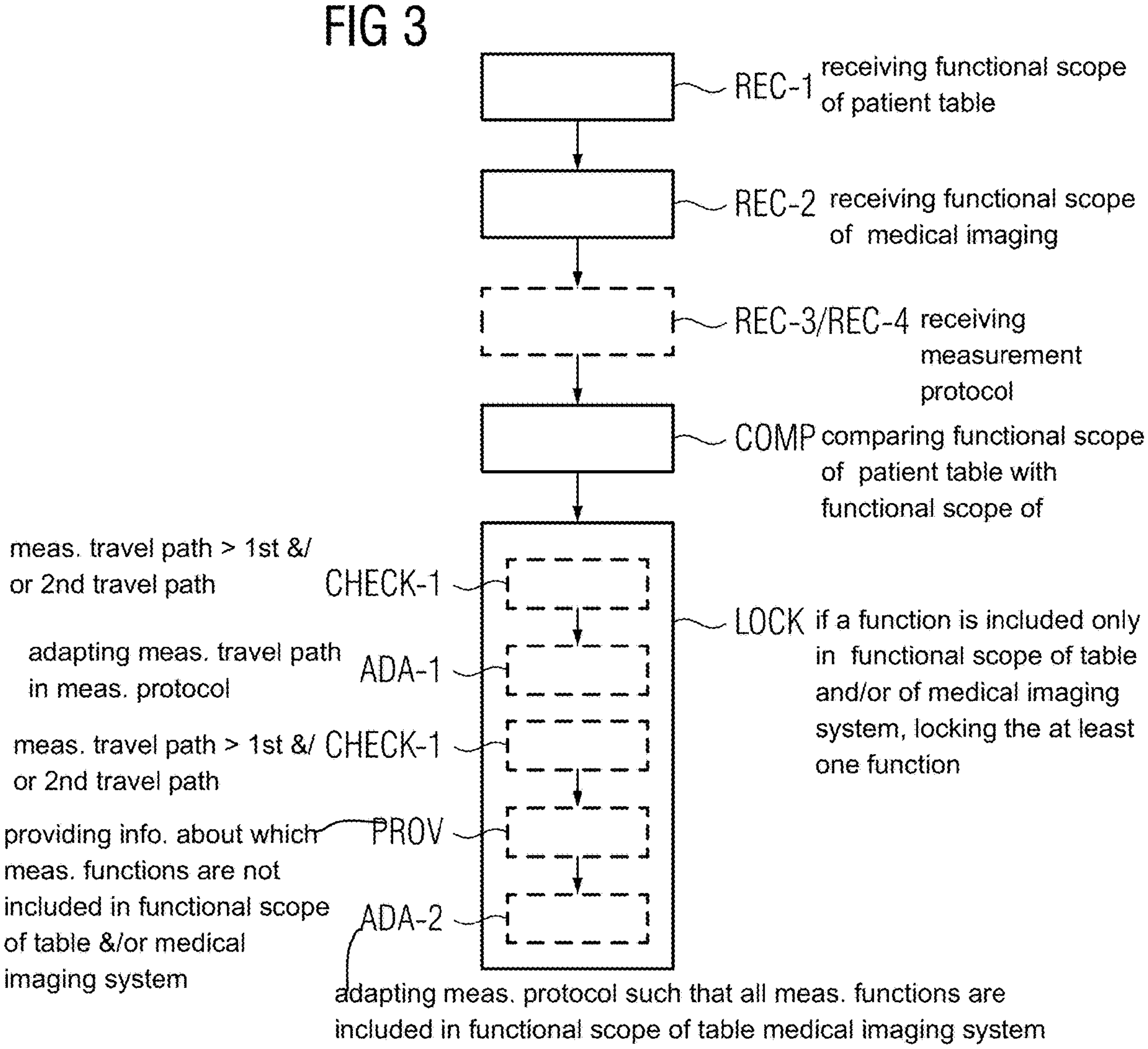

FIG 3

REC-1 receiving functional scope of patient table

REC-2 receiving functional scope of medical imaging

REC-3/REC-4 receiving measurement protocol

COMP comparing functional scope of patient table with functional scope of

LOCK if a function is included only in functional scope of table and/or of medical imaging system, locking the at least one function CHECK-1 meas. travel path > 1st &/ or 2nd travel path ADA-1 adapting meas. travel path in meas. protocol CHECK-1 meas. travel path > 1st &/ or 2nd travel path PROV providing info. about which meas. functions are not included in functional scope of table &/or medical imaging system ADA-2 adapting meas. protocol such that all meas. functions are included in functional scope of table medical imaging system

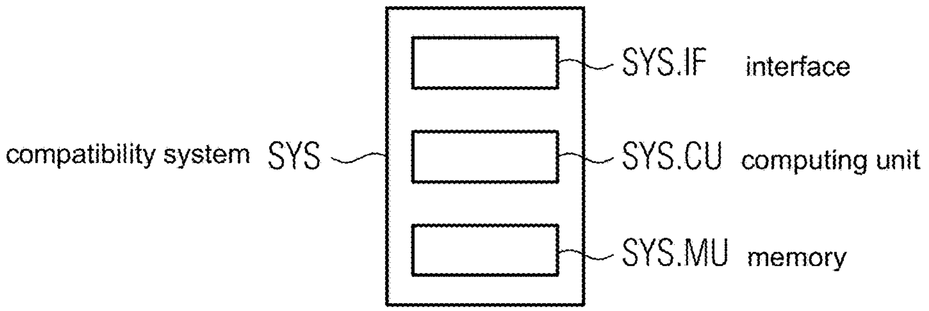

FIG 4

1
gradient control unit
19
RF antenna
cntrl unit
21
22
sys.cntl
unit
dis.
inp.
24
23
25
27
26
out
31
28
in
30
29
user console
11
16
36
28
37
12
17
32
13
14
38
15
Z
20
18
15b
base
10

COMPATIBILITY PRODUCTION OF A PATIENT TABLE AND A MEDICAL IMAGING SYSTEM

TECHNICAL FIELD

The present disclosure relates to a method for producing compatibility of a patient table and of a medical imaging system. The disclosure further relates to a compatibility system that is designed to execute the method. The disclosure further relates to a computer program product and a computer-readable storage medium.

BACKGROUND

In order to mount a patient during a medical examination or image acquisition with a medical imaging system, the patient is mounted or positioned on a patient table. The patient table is, in this case, typically designed to interact with the medical imaging system and to support functions of the medical imaging system. Thus, it is necessary for the functions supported by the patient table to correspond to or be supplemented by functions supported by the medical imaging system. The medical imaging system is designed to capture medical image data of the patient during the examination.

For example, one function of the patient table can specify a maximum travel path along which the patient can travel on the patient table. The medical imaging system can likewise specify a maximum travel path, which the medical imaging system supports in particular with its mechanical characteristics. Both these maximum travel paths must be compatible with one another in order to ensure firstly that the stability of the medical imaging system and the patient table is guaranteed throughout the examination and secondly that the examination can be performed as intended and the patient can be moved with the patient table into the corresponding positions.

The medical imaging system can, for example, be a magnetic resonance tomography (acronym: MRT) system. The patient table can then, for example, have a number of plugin locations for local coils. The number of local coils can then be read by the MRT system. In this example, the number and, in particular, the positions of plugin locations on the patient table must, therefore, correspond to the number and, in particular, the positions of readable local coils of the MRT system.

Many other functions, with respect to which the medical imaging system and the patient table must be compatible, are known.

It is known for a patient table to be designed specifically for use with a particular medical imaging system. The patient table thus supports the same functions as are also supported by the medical imaging system. Suppose a patient table is connected to a medical imaging system with which the patient table is not compatible. In that case, it is known that the use of the patient table in combination with the medical imaging system to be actively prevented.

However, in a medical facility, for example a hospital or a radiology practice, there is typically more than one medical imaging system in use. For reasons of time- and cost-efficiency, it would thus be desirable for a patient table to be compatible with or usable with different medical imaging systems. It is also known for a patient to have to be examined for particular examinations with more than one medical imaging system. To avoid relocating the patient to different patient tables, it is here too desirable for a patient table to be compatible with multiple medical imaging systems. This results firstly in time-saving, and secondly, the medical image data acquired with the different medical imaging systems can be more easily compared since the patient is mounted virtually identically on the different image data.

SUMMARY

It is, hence, the object of the present disclosure to provide a method that enables the flexible use of a patient table with different medical imaging systems or the use of different patient tables with one medical imaging system.

The object is achieved by a method for producing compatibility of a patient table and of a medical imaging system, by a compatibility system for producing compatibility of a patient table and of a medical imaging system, by a computer program product, and by a computer-readable storage medium in accordance with the independent claims.

Advantageous developments are set out in the dependent claims and the following description.

The inventive solution for the object is described below both in respect of the claimed devices and also in respect of the claimed method. Features, advantages or alternative forms of aspect mentioned here can likewise also be transferred to the other claimed subject matters and vice versa. In other words, the claims in question (which are, for example, directed at a device) can also be developed with the features described or claimed in connection with a method. The corresponding functional features of the method are, in this case, formed by the corresponding modules in question.

Independent of the grammatical term usage, individuals with male, female, or other gender identities are included within the term.

The disclosure relates to a computer-implemented method for producing compatibility of a patient table and a medical imaging system. In this case the patient table is designed to mount a patient during an examination with the medical imaging system. The method includes a method step of receiving a functional scope of the patient table. In this case, the functional scope of the patient table includes at least one function. The method further includes a method step of receiving a functional scope of the medical imaging system. In this case, the functional scope of the medical imaging system includes at least one function. The method further includes a method step of comparing the functional scope of the patient table with the functional scope of the medical imaging system. If at least one function is included only in the functional scope of the patient table and/or only in the functional scope of the medical imaging system, the method further includes a method step of locking this at least one function.

The medical imaging system is designed to examine a patient. In this case, in particular, the medical image data of the patient is captured. In particular, medical image data of part of the patient is captured. The medical image data, in this case, includes a (partial) acquisition of the patient.

The medical imaging system supports at least one function. This at least one function is included in the functional scope of the medical imaging system. In this case, the function can be designed to capture the medical image data. The function can, for example, include a travel path of the patient table for the capture of the medical image data, interfaces with the patient table, etc.

The functional scope of the medical imaging system can, in some aspects of the disclosure, be received by means of a unique identifier. The identifier is unique with respect to the medical imaging system and indicates the functional scope of the medical imaging system. The identifier can, in particular, be electronic or mechanical. Alternatively, the functional scope can be received by means of a communication protocol.

The patient can in this case, in particular, be a person, an animal, a phantom, or any other object.

The patient table is designed to mount or position a patient during an examination with the medical imaging system. The patient table is, in particular, designed to introduce the patient into the medical imaging system. In particular, the patient table is designed to introduce the patient into an opening in the medical imaging system.

The patient table supports at least one function. The at least one function is in this case, included in the functional scope of the patient table. The function can, for example, include a travel path of the patient table for the capture of the medical image data, interfaces with the medical imaging system, etc.

In the method step of receiving the functional scope of the patient table, information is received about which functions the patient table supports. The functional scope of the patient table, in this case, includes at least one function.

In some aspects of the disclosure the functional scope of the patient table can be received by means of a unique identifier. The identifier is unique with respect to the patient table and indicates the functional scope of the patient table. The identifier can, in particular, be electronic or mechanical. Alternatively, the functional scope can be received by means of a communication protocol.

In the method step of receiving the functional scope of the medical imaging system, information is received about which functions are supported by the medical imaging system. The functional scope of the medical imaging system includes at least one function.

In the method step of comparing the functional scope of the patient table and the functional scope of the medical imaging system, the functions included in the respective functional scopes are compared. In particular, a check is made to see whether one or more functions are included only in one of the functional scopes. In other words, a check is made to see whether the at least one function included in the functional scope of the patient table is also included in the functional scope of the medical imaging system. Likewise, a check is made to see whether the at least one function included in the functional scope of the medical imaging system is also included in the functional scope of the patient table. In particular, a check is made to see whether a characteristic of a function included in the functional scopes is identical.

If at least one function is included in only one of the two functional scopes and/or is characterized by a function included in both functional scopes, this at least one function is locked in the method step of locking the at least one function. In other words, if the at least one function which is included in the functional scope of the patient table is not included in the functional scope of the medical imaging system, this function is locked on the patient table. Likewise, the at least one function is locked on the medical imaging system if the at least one function is included only in the functional scope of the medical imaging system but not in the functional scope of the patient table. Likewise, the function is locked if the function is indeed included in both functional scopes but with different characteristics. A characteristic can, for example, be defined by a route of a travel path. In this case, both functional scopes can include a function that defines a travel path, but these may be different.

Locking, in this case, means that the locked function can no longer be executed or used. For example, an interface can be deactivated by the locking.

Alternatively, the locking can mean that a function is restricted or can be used only in part or in a restricted form. This occurs in particular if the characteristic of a function is different in the functional scopes. For example, a travel path can be restricted by the locking.

The inventor has recognized that by comparing the functional scopes, it is possible to establish which functions are supported by only one of the two components: the medical imaging system or the patient table. The inventor has recognized that by locking the functions that are supported by only one of the two components, it is possible to prevent functions being used that are not supported by both components and, thus, a faulty examination from being performed or the examination from being aborted and interpreted as a malfunction. Additionally, thanks to the comparison, it is possible to establish whether a function has different characteristics in both the functional scopes. By locking the corresponding function, the function can be restricted to the respective component, the patient table, or the medical imaging system, such that the functional characteristics of both components are adapted to one another.

According to one aspect of the disclosure, the patient table is mobile.

The patient table is thus designed to be mobile. The patient table is, in this case, comprised of a patient positioning device. The patient positioning device is designed to move the patient table along the travel path. The patient positioning device also includes a base with which the patient table is held. In the case of the mobile patient table, this base is designed to be movable. In this way the patient table can be moved to different medical imaging systems. The mobile patient table can, in particular, be moved along a rail system or by means of rollers.

The inventor has recognized that thanks to the flexible compatibility with different medical imaging systems, the patient table is advantageously designed to be mobile. The inventor has recognized that in this way the mobile patient table can be used with different medical imaging systems and can be moved or can travel to these. The inventor has recognized that in this way, operational sequences in a medical facility can be accelerated or optimized. In particular, it is not necessary to reposition a patient who is to be examined with different medical imaging systems. In addition, it is not necessary to wait until a particular patient table is free for a medical imaging system since another patient table can also be used with the medical imaging system. In addition, a patient can already be prepared for the examination with the medical imaging system on a patient table while another patient is still being examined on another patient table with the medical imaging system. In this way idle times of the medical imaging system can be reduced or prevented.

In accordance with another aspect of the disclosure, the medical imaging system is a magnetic resonance tomography system.

The magnetic resonance tomography (acronym: MRT) system preferably includes a medical and/or diagnostic magnetic resonance device that is designed and/or embodied to capture medical and/or diagnostic image data, in particular medical and/or diagnostic MRT image data, of a patient. To this end, the magnetic resonance device includes a scanner unit. The scanner unit of the magnetic resonance device preferably includes a detector unit, in particular a magnet unit, to capture the medical and/or diagnostic image data. The scanner unit, in particular the magnet unit, advantageously in this case includes a body coil or a base magnet, a gradient coil unit and a radio-frequency antenna unit. The radio-frequency antenna unit is permanently arranged inside the scanner unit and is designed and/or embodied to transmit an excitation pulse. To capture the magnetic resonance signals, the magnetic resonance device can have local radio-frequency coils or local coils, which are arranged around the region of the patient to be examined.

The body coil or the base magnet of the scanner unit is designed to generate a homogeneous constant magnetic field with a defined and/or determined magnetic field strength, such as, for example, with a defined and/or determined magnetic field strength of 3 T or 1.5 T, etc. In particular, the base magnet is designed to generate a strong, constant, and homogeneous constant magnetic field. The homogeneous constant magnetic field is preferably arranged and/or can be found inside the patient receiving area of the magnetic resonance device. The gradient coil unit is designed to generate magnetic field gradients, which are used for position encoding during imaging.

The patient receiving area is designed and/or embodied to receive the patient, in particular the area of the patient to be examined, for a medical magnetic resonance examination or examination. For example, to this end, the patient receiving area is designed to be cylindrical and/or cylindrically surrounded by the scanner unit. To this end, the scanner unit has a casing of the housing unit, which at least partially surrounds the patient receiving area. The casing surrounding the patient receiving area can, in this case, also be formed in one piece and/or integrally with the side of the radio-frequency antenna unit of the scanner unit facing the patient receiving area or can also be designed to be separate from the radio-frequency antenna unit of the scanner unit.

If the patient is moved into the MRT system or the body coil, said patient is, in particular, positioned in the patient receiving area.

A field of view (FOV) and/or an isocenter of the magnetic resonance device is preferably arranged inside the patient receiving area. The FOV preferably includes a capture area of the magnetic resonance device, inside which the conditions for capturing medical image data, in particular MRT image data, are present, such as, for example, a homogeneous constant magnetic field. The isocenter of the magnetic resonance device preferably includes the area and/or point inside the magnetic resonance device which has the optimum and/or ideal conditions for capturing medical image data, in particular magnetic resonance image data. In particular, the isocenter includes the most homogeneous magnetic field area inside the magnetic resonance device.

The patient positioning device is designed to position and/or mount the patient for an examination. The patient positioning device, in this case, includes the patient table, which is designed to be able to be introduced into the patient receiving area. For a magnetic resonance examination, the patient is positioned on the patient table such that the area to be examined is arranged and/or positioned inside the isocenter of the patient receiving area after the patient table has been positioned or moved along the travel path inside the patient receiving area.

For communication and/or exchange of the patient's information with the medical operative during an examination, the magnetic resonance device has a communication unit. On the user side, the communication unit preferably has a communication element, for example, a communication console to input and/or output communication data, for example, information. Furthermore, on the patient side the communication unit likewise has at least one communication element. In particular, the communication unit has an acoustic and/or visual communication element. The acoustic communication element can, for example, be a loudspeaker or a microphone. The visual communication element can, for example, be a screen, in particular a touch-sensitive screen.

The inventor has recognized that the method can, in particular, be used for the compatibility of a patient table with an MRT system. Idle times, in which no patient is being examined, are especially expensive in the case of an MRT system and can be reduced with this method. In addition, different MRT systems have particularly many different functions, which in turn must be compatible with different patient tables. The inventor has recognized that in order to obtain the aforementioned advantages the method can be applied particularly advantageously for the MRT system.

In accordance with a further aspect of the disclosure the at least one function included in the functional scope of the patient table and/or in the functional scope of the medical imaging system relates to one of the following functions: travel path, number of plugin locations for local coils, transmission path for a local coil, support for local shim coils, maximum patient weight supported, connection for a vacuum cushion, connection for a patient communication system, interfaces to other systems.

The travel path as a function of the patient table indicates how far the patient table can be moved. In particular, the travel path as a function of the patient table indicates how far the patient table can be moved relative to its base. The travel path can, in this case, be delimited by the mechanical stability of the patient positioning device and/or a patient's weight and/or a weight of an accessory that is used on the patient table.

The travel path as a function of the medical imaging system indicates how far the patient table can be moved into the medical imaging system. The travel path is, in this case, restricted by a design of a support structure and/or the weight of the patient on the patient table.

The number of plugin locations for local coils as a function of the patient table indicates how many local coils can be connected to the patient table. In particular, the number of plugin locations as a function of the patient table indicates where the plugin locations are positioned on the patient table.

The number of plugin locations for local coils of the MRT system indicates how many local coils can be read by the MRT system or the signals of how many local coils can be used for the reconstruction of the medical image dataset. In particular, the number of plugin locations as a function of the MRT system indicates where the readable plugin locations for local coils have to be positioned on the patient table.

The transmission path for a local coil as a function of the patient table indicates whether a connection is provided in the patient table, by means of which a local coil can be used to transmit a signal. The connection is, in this case, designed to transmit the transmission signal.

The transmission path for a local coil as a function of the medical imaging system, in this case, indicates whether the medical imaging system is designed to provide a signal that can be sent via the connection of the patient table to the corresponding local coil and can be transmitted thereby.

The support for local shim coils as a function of the patient table indicates whether local shim coils can be connected to the patient table and, if so, how many.

The support for local shim coils as a function of the medical imaging system indicates whether and, if so, how many signals can be provided for local shim coils with the medical imaging system.

The maximum supported patient weight as a function of the patient table indicates the maximum permitted weight of the patient on the patient table. In other words, the maximum supported patient weight, in this case, indicates the maximum patient weight for which the patient table is designed. In particular, the maximum patient weight, in this case, indicates the maximum patient weight for which the mechanical stability of the patient table is designed even when the patient table is moved and provides sufficient stability.

The maximum supported patient weight as a function of the medical imaging system indicates the maximum permitted weight of a patient who is to be examined with the medical imaging system. The maximum patient weight, in this case, depends in particular on a support structure of the medical imaging system. The support structure supports the patient table during the movement in the medical imaging system.

The connection for a vacuum cushion as a function of the patient table indicates whether and, if so, where and how many vacuum cushions can be connected for mounting the patient onto the patient table.

Analogously, the connection for a vacuum cushion as a function of the medical imaging system indicates whether and, if so, where and how many vacuum cushions can be supported for mounting the patient during the capture of the medical image dataset.

The connection for a patient communication system as a function of the patient table, in this case, indicates which communication systems are supported by the patient table. The communication systems, in this case, serve to divert the patient during the examination. In addition or alternatively, the communication systems serve to establish contact with the patient during the examination, since typically, the medical operative is located in another room during the examination, in other words, separate from the patient. The patient communication system can, for example, include a wired or wireless alarm ball and/or a headset and/or a microphone and/or a screen, etc. The connection for a patient communication system, in this case, indicates which of these communication systems can be connected to the patient table and which corresponding signals can be transmitted.

The connection for a patient communication system as a function of the medical imaging system, in this case, indicates which of the possible aforementioned communication systems can be connected to the medical imaging system and what signals can be transmitted.

The interfaces to other systems as a function of the patient table indicate which other systems can be connected to the patient table. In particular, it can, in this case, be indicated whether the patient table includes a connection or an interface for an electrocardiogram system (acronym: EKG system).

The interfaces to other systems as a function of the medical imaging system indicate which other systems can be connected to the medical imaging system and, in particular, the signals of which other systems can be processed by the medical imaging system and/or to which other systems the medical imaging system can provide a signal. For example, the interfaces to other systems can indicate whether the medical imaging system is designed to capture an EKG-triggered image dataset, or to perform an EKG-triggered examination and can further process the signal of an EKG system for this.

The inventor has recognized that there are a variety of functions that must be compatible between a medical imaging system and a patient table in order to be able to use both with one another. In particular, the functions must be compatible in order to ensure safe and error-free use.

In accordance with a further aspect of the disclosure, the functional scope of the patient table includes a function that indicates a first number of plugin locations for local coils. In this case, the functional scope of the medical imaging system includes a function that indicates a second number of plugin locations for local coils. In this case, the first number is larger than the second number. In this case, locking includes a method step of locking the plugin locations on the patient table, which are not indicated by the function included in the functional scope of the medical imaging system.

A local coil is designed to capture and provide a signal or data during the examination. The medical imaging system can then read the data of the local coils and, based thereon, can ascertain the medical image data.

The first number of plugin locations for local coils indicates how many local coils can be connected to the patient table. In particular, the first number of plugin locations indicates a position of the plugin locations on the patient table. In this case, each plugin location is assigned a particular position on the patient table. The second number of plugin locations for the local coils indicates how many local coils can be connected to the medical imaging system and thus can be read thereby. During reading, data captured by the local coils is read. In particular, the second number of plugin locations indicates from which positions on the patient table a local coil can be connected to the medical imaging system or from which positions on the patient table the captured data can be read. If the first number is larger than the second number, this means that more local coils can be connected to the patient table than can be read by the medical imaging system. In particular, in this case plugin locations on the patient table are arranged or positioned at positions that cannot be read by the medical imaging system. In the method step of locking, the number of plugin locations on the patient table that are locked means that the number of non-locked plugin locations on the patient table corresponds to the second number of plugin locations. In other words, the number of plugin locations on the patient table that are locked means that the maximum number of local coils that can be connected to the patient table is equal to the number that can be read by the medical imaging system. In particular, in this case, those plugin locations on the patient table are locked and are arranged at positions on the patient table that cannot be read by the medical imaging system.

Locking, in this case, means that no data is read from a local coil or is supplied to a local coil that is connected to a locked plugin location.

In particular, a medical operative can be shown the maximum number of available plugin locations, i.e., the number of non-locked plugin locations. In particular, the medical operative can be shown which plugin locations are or are not locked. This can be displayed on a user interface. In particular, this can be done using a display device, for example a monitor or a screen.

During locking, those plugin locations on the patient table are advantageously locked and are positioned such that they cannot be connected to the medical imaging system or cannot be read thereby, since the position of these plugin locations is not included in the functional scope of the medical imaging system.

Alternatively, during locking in particular a sequence can be specified in which plugin locations on the patient table are locked. For example, if the first number is larger by one than the second number, plugin location A is locked. If the first number is larger by two than the second number, plugin location A is initially locked and additionally plugin location B, etc.

Alternatively, those plugin locations can be locked to which a local coil is to be connected last or to which no local coil is connected. For example, a medical operative can connect several local coils to the patient table one after the other. As soon as the number of connected local coils exceeds the second number, the plugin locations on the patient table that are still free are locked.

The inventor has recognized that by locking, it is possible to prevent a local coil from being connected to a position on the patient table that cannot be read by the medical imaging system. In this way, it can be ensured that a patient table, which can move such that a whole-body acquisition of the patient mounted on the patient table can be captured, is also compatible with a medical imaging system that only supports a travel path in which merely a partial-body acquisition of the patient can be captured. In addition, the inventor has recognized that by locking, it is possible to prevent too many local coils from being connected and the medical imaging system from being unable to read the data captured by the local coils and thus being lost. This could result in the examination being faulty since not all captured data can be read. By locking the corresponding plugin locations, it is thus possible to ensure that the data captured with the local coils can also, in fact, be read and can be used to ascertain the medical image data.

In accordance with a further aspect of the disclosure, the functional scope of the patient table includes a function that indicates the first maximum travel path of the patient table. In addition, the functional scope of the medical imaging system includes a function that indicates a second maximum travel path of the patient table. In this case, the first maximum travel path is larger than the second maximum travel path. In this case, locking includes a method step of restricting an actuation of the patient table such that the patient table can only be moved along the second maximum travel path.

The first maximum travel path of the patient table indicates the maximum distance the patient table can be moved along a travel path for an examination. In this case, the first maximum travel path can, in particular, indicate the maximum distance the patient table can move in a direction relative to its base. The first maximum travel path is, in this case, independent of the mobility of the patient table by means of its base in the form of a mobile patient table. The first maximum travel path serves to introduce the patient table into the medical imaging system.

The second maximum travel path indicates the maximum distance any patient table can be introduced into the medical imaging system. The second maximum travel path can, in particular, be specified by a support structure of the medical imaging system, which defines the mechanical stability of the medical imaging system when the patient table is moved. Alternatively or additionally, the second maximum travel path can depend on the weight of the patient.

When restricting the actuation of the patient table, the actuation is restricted such that the patient table can be introduced into the medical imaging system by a maximum of the second maximum travel path.

In this case, in particular, a movement of the patient table into the medical imaging system can be terminated if the path already traveled exceeds the second maximum travel path.

In particular, it is possible to display to a medical operative that the travel path of the patient table is restricted to the second maximum travel path. As described above, this can be displayed via a user interface, in particular by means of a display device, for example a screen or a monitor.

The inventor has recognized that by restricting the travel path of the patient table or the actuation of the patient table such that the patient table can be moved by a maximum of the second maximum travel path, it is guaranteed that the stability of the medical imaging system is ensured. In other words, in this way, the patient table can be prevented from being introduced too far into the medical imaging system, which can result in instability and possibly in damage to the medical imaging system and, in the worst case in, injury to the patient.

In accordance with a further aspect of the disclosure, the functional scope of the patient table includes a function that indicates the first maximum travel path of the patient table. In addition, the functional scope of the medical imaging system includes a function that indicates a second maximum travel path of the patient table. In this case, the first maximum travel path is not equal to the second maximum travel path. In this case the method also includes a method step of receiving a measurement protocol. In this case the measurement protocol specifies a measurement travel path required for the performance of the examination with the medical imaging system. In this case locking includes a method step of checking whether the measurement travel path is larger than the first and/or second maximum travel path. In this case, locking also includes a method step of adapting the measurement travel path in the measurement protocol so that the measurement travel path corresponds to the smaller of the first or the second maximum travel path.

The first and the second maximum travel paths are, in this case, in particular, formed as described above.

The measurement protocol is designed to perform or initiate the examination with the medical imaging system. The measurement protocol includes functions that are necessary for the examination. In particular, the measurement protocol defines the measurement parameters of these functions, which are required for the performance of the examination. In particular, the measurement travel path is defined in the measurement protocol in the form of a measurement function. The measurement travel path indicates the maximum distance the patient has to be introduced into the medical imaging system for the examination.

In the method step of receiving the measurement protocol, the measurement protocol can, in particular, be received from a database. The measurement protocol can thus, in particular, be stored in the database and received if the examination is to be performed. Alternatively, the measurement protocol can be received from a user interface. A medical operative can create and/or adapt the measurement protocol at the user interface.

In the method step of checking whether the measurement travel path is larger than the first and/or second maximum travel path, the measurement travel path is compared to the first and the second maximum travel path.

In the method step of adapting the measurement travel path, the measurement travel path is adapted in the measurement protocol if the measurement travel path is larger than at least the first maximum travel path or the second maximum travel path. In this case, the measurement travel path is adapted such that the adapted measurement travel path corresponds to the smaller of the first or second maximum travel path. In particular, it is ensured in this case that during the examination, the patient table is displaced by a maximum of the smallest of the following values: measurement travel path, first maximum travel path, and second maximum travel path.

In addition, the information that the measurement travel path has been adapted can be displayed to the medical operative. This information about the adaptation of the measurement travel path can, in particular, be displayed by means of the above-described user interface. This information about the adaptation of the measurement travel path can, in particular, be displayed by means of the above-described display device.

The inventor has recognized that by adapting the measurement protocol it can be ensured that the stability of the patient table and the medical imaging system is ensured at all times. In other words, it is ensured that the patient table is not moved too far into a position that is no longer supported by the patient table and/or by the medical imaging system. The inventor has recognized that in this way the compatibility of the measurement protocols can also be ensured. This is, in particular, necessary if universal measurement protocols are stored, for example, in a database, which have to be adapted to a corresponding combination of patient table and medical imaging system.

In accordance with a further aspect of the disclosure the method also includes a method step of receiving a measurement protocol. In this case the measurement protocol includes measurement functions necessary for the performance of the examination with the medical imaging system. In this case locking includes a method step of checking whether at least one of the measurement functions is not included in the functional scope of the patient table and/or in the functional scope of the medical imaging system. In this case locking also includes a method step of providing information about which of the measurement functions is not included in the functional scope of the patient table and/or in the functional scope of the medical imaging system.

The measurement protocol includes measurement functions that are required or used for the performance of the examination. In particular, the measurement protocol defines the measurement parameters of these measurement functions. In this case, the measurement function specifies a function of the patient table and/or of the medical imaging system required for the examination. The measurement parameter can then define a configuration of this function or specify a value for the functionality.

In the method step of receiving the measurement protocol, the measurement protocol is received as described above.

In the method step of checking whether at least one of the measurement functions is not included in the functional scope of the patient table and/or in the functional scope of the medical imaging system, a check is made to see whether each of the measurement functions is included in the functional scope of the patient table and in the functional scope of the medical imaging system.

In the method step of providing information about which of the measurement functions is not included in the functional scope of the patient table and/or in the functional scope of the medical imaging system, information is provided about the result of the method step of checking. In particular, the information is used to show which measurement function is not included in the functional scope of the patient table and in the functional scope of the medical imaging system.

The information is, in particular, provided to the medical operative. The information can in this case in particular be provided by means of a user interface, in particular via an operator interface. The information can, in particular, be displayed by means of a display device. The display device can, in this case, in particular, be a monitor or a screen.

In this way, it is possible to identify the measurement functions in a measurement protocol that cannot be used. In particular, these measurement functions cannot be used since the corresponding functions of the patient table or of the medical imaging system are locked or are not included in the corresponding functional scope.

In accordance with one aspect of the disclosure, locking also includes a method step of adapting the measurement protocol such that the measurement functions are adapted so that all measurement functions are included in the functional scope of the patient table and in the functional scope of the medical imaging system.

The adaptation can, in particular, take place automatically, in that a measurement function that is not included in the functional scopes of the medical imaging system and of the patient table is replaced by an equal or equivalent function that is included in both the functional scopes.

Alternatively, the adaptation can take the form of a request to the operative to adapt, replace, or remove the corresponding measurement function, which is not included in both functional scopes, so that the adapted measurement function is included in both functional scopes. The request can be provided via the above-described user interface, operator interface, or display device.

Alternatively, a suitable different measurement protocol can be received in the method step of adaptation. The method steps of checking whether at least one of the measurement functions of the newly received measurement protocol is not included in both functional scopes, of providing the information about the result of the check, and, if appropriate, of the adaptation are performed analogously for the newly received measurement protocol.

In this way it can be ensured that the desired examination can be performed with the available functional scope of the patient table and the medical imaging system. The inventor has recognized that in this way an occurrence of errors can be prevented or reduced.

The disclosure also relates to a compatibility system for producing compatibility of a patient table and a medical imaging system. In this case the patient table is designed to support a patient during an examination with the medical imaging system. The compatibility system includes an interface and a computing unit which is designed to execute the following method steps: receiving a functional scope of the patient table, wherein the functional scope of the patient table includes at least one function; receiving a functional scope of the medical imaging system, wherein the functional scope of the medical imaging system includes at least one function; comparing the functional scope of the patient table to the functional scope of the medical imaging system; and if at least one function is included only in the functional scope of the patient table and/or only in the functional scope of the medical imaging system, locking the at least one function.

Such a compatibility system can, in particular, be designed to execute the above-described method for producing compatibility of a patient table and of a medical imaging system and aspects thereof. The compatibility system is designed to execute this method and aspects thereof in that the interface and the computing unit are designed to execute the corresponding method steps.

The disclosure also relates to a computer program product with a computer program and to a computer-readable medium. A largely software-based implementation has the advantage that even compatibility systems already in use hitherto can easily be retrofitted by a software update in order to work in the manner described. Such a computer program product can, where necessary, comprise, besides the computer program, additional elements such as example, documentation, and/or additional components, as well as hardware components, such as hardware keys (dongles, etc.) for the use of the software.

In particular, the disclosure also relates to a computer program product with a computer program that can be loaded directly into the memory of a compatibility system, with program sections in order to execute all steps of the above-described method for producing compatibility of a patient table and of a medical imaging system and aspects thereof, if the program sections are executed by the compatibility system.

In particular, the disclosure relates to a computer-readable storage medium, on which are stored program sections that can be read and executed by a compatibility system in order to execute all steps of the above-described method for producing compatibility of a patient table and of a medical imaging system and aspects thereof, if the program sections are executed by the compatibility system.

The above-described properties, features and advantages of this disclosure will become clearer and more understandable in connection with the following figures and the descriptions thereof. In this case, the figures and descriptions should in no way restrict the disclosure and the forms of aspect thereof.

BRIEF DESCRIPTION OF THE DRAWINGS

Identical components are provided with corresponding reference characters in different figures. The figures are generally not true to scale.

In the drawings:

FIG. 3 shows a third exemplary aspect of a method for producing compatibility of a patient table and of a medical imaging system, FIG. 4 shows a compatibility system for producing compatibility of a patient table and of a medical imaging system.

DETAILED DESCRIPTION

Figure 1:
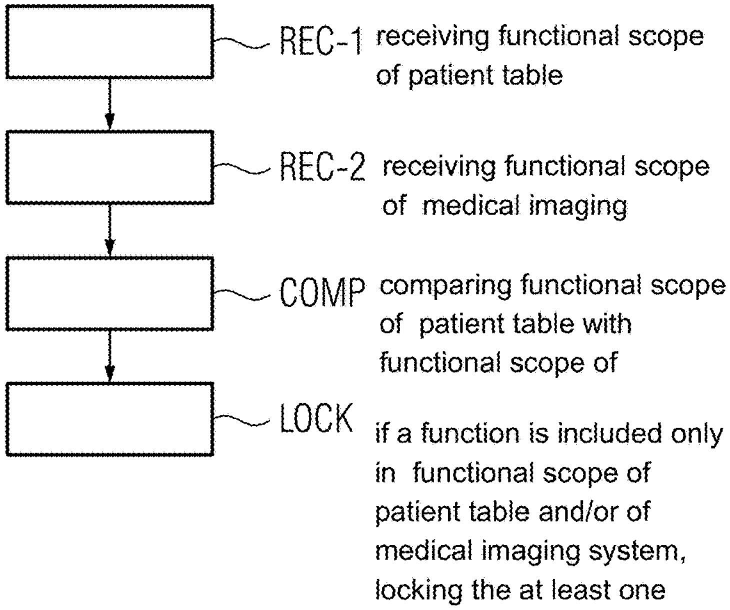
FIG. 1 shows a first exemplary aspect of a method for producing compatibility of a patient table and of a medical imaging system.

FIG. 1 shows a first exemplary aspect of a method for producing compatibility of a patient table 15 and of a medical imaging system.

The patient table 15 is, in this case, designed to mount or position a patient 13 during an examination with the medical imaging system. In particular, the patient table 15 is designed to introduce the patient 13 into the medical imaging system for the examination. For this, a reclining area of the patient table is moved relative to a base 15*b* of the patient table 15.

The patient table 15 can, in particular, be designed to be mobile. A mobile patient table 15 is designed to travel back and forth between different medical imaging systems. In particular, the patient table 15 can, in this case, move by means of its base 15*b*. In particular, the mobile patient table 15 can be designed so that it can move along a rail system or by means of a roller system.

The medical imaging system is designed to capture a medical image dataset of the patient 13 mounted on the patient table 15 during an examination.

In some aspects of the disclosure, the medical imaging system can, in particular, be a magnetic resonance tomography (acronym: MRT) system 1. One form of aspect of an MRT system 1 is described in FIG. 5.

In the method step of receiving REC-1, a functional scope of the patient table 15, the functional scope is received, which includes the functions supported by the patient table 15. In this case the functional scope of the patient table 15 includes at least one function. The functional scope of the patient table 15 can be transmitted by means of an electrical or mechanical identifier or by means of a communication protocol.

In a method step of receiving REC-2 a functional scope of the medical imaging system, the functional scope is received, which includes the functions supported by the medical imaging system. In this case, the functional scope of the medical imaging system includes at least one function. The functional scope of the medical imaging system can be transmitted by means of an electrical or mechanical identifier or by means of a communication protocol.

The functions of the functional scopes of the patient table 15 or of the medical imaging system can, for example, relate to mechanical functional parameters and/or interfaces, etc.

In particular, the at least one function included in the functional scope of the patient table 15 and/or of the medical imaging system can relate to one of the following functions: travel path, number of plugin locations for local coils, transmission path for a local coil, support for local shim coils, maximum supported patient weight, connection for a vacuum cushion, connection for a patient communication system, interfaces to other systems.

The travel path, in this case, indicates the maximum distance the patient Table 15 can be introduced into the medical imaging system. In this case, the maximum travel path is restricted by a mechanism of the patient table 15 and/or by a support structure of the medical imaging system and/or by the weight of the patient 13 and/or by a spatial arrangement of the medical imaging system. The maximum travel path of the patient table 15 can sometimes differ from the maximum travel path of the medical imaging system. The functional scopes then include various functions with respect to the maximum travel path.

The number of plugin locations for local coils indicates how many plugin locations the patient table includes or how many plugin locations the medical imaging system includes. In particular, the number of plugin locations for local coils specifies a position for these plugin locations on the patient table. In this case, each plugin location is assigned a position on the patient table. If the patient table and the medical imaging system include different numbers of plugin locations, the respective functions relating to the plugin locations of the respective functional scopes are different.

A local coil is used in an MRT system for receiving signals.

The transmission path for a local coil indicates whether one of the local coils, for which a plugin location is available, can also be used as a transmission coil. For this, the corresponding plugin location is fitted with a transmission path, in other words, a line for the transmission signal. If the patient table includes the function of the transmission path for the local coil, the corresponding line to the corresponding plugin location in the patient table 15 is provided or designed. If the medical imaging system includes the function of the transmission path for the local coil, the medical imaging system is designed to provide the corresponding signal for transmission by means of the local coil.

The support for local shim coils indicates whether a local shim coil is supported and, if so, how many.

The maximum supported patient weight indicates the maximum permitted weight of the patient positioned on the patient couch. The maximum supported patient weight can, in particular, influence the maximum travel path. If the functional scope of the patient table 15 and the functional scope of the medical imaging system specify different maximum patient weights, the functions in question are also different.

The function with respect to the connection of a vacuum cushion indicates whether the patient table or the medical imaging system supports the use of a vacuum cushion.

The function of connecting a patient communication system indicates what forms of patient communication can be connected to the patient table or the medical imaging system or for which forms of patient communication a signal can be provided and/or received. The patient communication system can, for example, include a display device and/or a headset and/or a microphone, and/or an alarm ball (wired or wireless). These all describe forms of patient communication.

The functions with respect to the interfaces to other systems indicate which interfaces are provided for a connection to a different system. Such a different system can be an EKG system, for example. The patient table 15 can be designed to receive an EKG signal, which is measured with an EKG system if it includes a corresponding interface. The medical imaging system can be designed to further process the EKG signal and, where appropriate, to adapt the examination to the EKG signal if it has the corresponding interface.

In a further method step of comparing COMP, the functional scope of the patient table 15 is compared to the functional scope of the medical imaging system. In particular, a check is made in this case to see whether a function is included in only one of the two functional scopes.

If during comparing COMP at least one function is included only in the functional scope of the patient table 15 or only in the functional scope of the medical imaging system, this at least one function is locked in a method step of locking LOCK. A locked function can no longer be used or executed. Alternatively, locking a function represents a restriction of the function. The locked function can then still be used only on a restricted basis.

Figure 2:
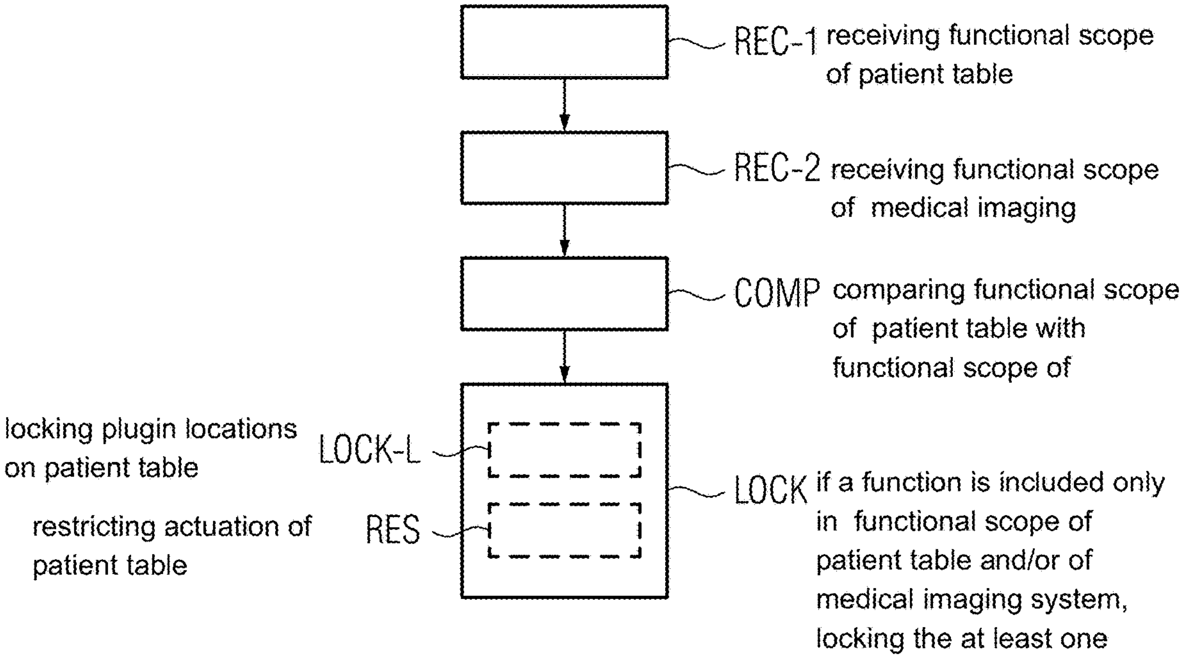
FIG. 2 shows a second exemplary aspect of a method for producing compatibility of a patient table and of a medical imaging system.

FIG. 2 shows a second exemplary aspect of a method for producing compatibility of a patient table 15 and of a medical imaging system.

The method steps of receiving REC-1 a functional scope of the patient table 15, of receiving REC-2 a functional scope of the medical imaging system, of comparing COMP the functional scope of the patient table 15 and the functional scope of the medical imaging system and of locking LOCK a function based on the comparison COMP are executed in accordance with the description for FIG. 1.

In accordance with the exemplary aspect, the functional scope of the patient table 15 can indicate a first number of plugin locations for local coils, and the functional scope of the medical imaging system can indicate a second number of plugin locations for local coils. The first number can, in this case, be larger than the second number.

In particular, the first number, in this case, specifies, for each plugin location on the patient table 15, a position on the patient table. In particular, the second number, in this case, specifies each plugin location that is connected to the medical imaging system or can be read thereby, where this can be positioned on the patient table.

The method step of locking LOCK then includes a method step of locking LOCK-L the plugin locations on the patient table 15 which are not indicated in the functional scope of the medical imaging system. The locked plugin locations are, in this case, deactivated. This means that no signal is received from these plugin locations and no signal is provided.

If, in each case, the positions of the plugin locations are included or indicated by the first and the second number, then during locking LOCK, those plugin locations on the patient table 15 are locked whose position is not indicated by the second number. In other words, depending on their position on the patient table 15 those plugin locations are locked, which are not connected to the medical imaging system and/or cannot be read thereby, since the corresponding position is in accordance with the functional scope of the medical imaging system is not supported by the medical imaging system.

In some aspects of the disclosure, a sequence can be provided in which the plugin locations on the patient table 15 are deactivated. Alternatively, the plugin locations that are connected last or that remain after connecting the local coils can be deactivated.

Alternatively or additionally, the functional scope of the patient table 15 includes a first maximum travel path of the patient table 15, and the functional scope of the medical imaging system includes a second maximum travel path of the patient table 15. In this case, the first maximum travel path can be larger than the second maximum travel path. If this is the case, locking LOCK includes a method step of restricting RES an actuation of the patient table 15 such that the patient table 15 can only maximally be moved along the second maximum travel path.

FIG. 3 shows a third exemplary aspect of a method for producing compatibility of a patient table 15 and of a medical imaging system.

The method steps of receiving REC-1 a functional scope of the patient table 15, of receiving REC-2 a functional scope of the medical imaging system, of comparing COMP the functional scope of the patient table 15 and the functional scope of the medical imaging system and of locking LOCK a function based on the comparison COMP are executed in accordance with the description for FIG. 1.

The third exemplary aspect can, in particular, also be combined with the second exemplary aspect.

In accordance with the exemplary aspect, the functional scope of the patient table 15 indicates a first maximum travel path of the patient table 15, and the functional scope of the medical imaging system indicates a second maximum travel path of the patient table 15.

The method includes a method step of receiving REC-3 a measurement protocol. The measurement protocol is designed to control the medical imaging system and the patient table 15 during the performance of the examination. The measurement protocol, in this case in particular, includes measurement functions that describe, specify, or indicate functions required for the examination. When receiving the measurement protocol, in particular, is received from a database. A plurality of measurement protocols can be stored or saved in the database. Alternatively, the measurement protocol can be provided by a user interface. In this case, the medical operative can define and provide the measurement protocol via the user interface.

Locking LOCK in this case includes a method step of checking CHECK-2 whether at least one of the measurement functions is not included in the functional scope of the patient table 15 and/or the functional scope of the medical imaging system. In other words, a check is made to see whether all measurement functions are included in the functional scope of the patient table 15 and in the functional scope of the medical imaging system. If this is not the case, locking LOCK includes a further method step of providing PROV information about which of the measurement functions is not included in the functional scope of the patient table and/or in the functional scope of the medical imaging system. This information can, in this case, in particular, be provided to a medical operative.

Locking LOCK can optionally also include a method step of adapting ADA-2 the measurement protocol. In this case the measurement protocol is adapted such that all measurement functions are included in the functional scope of the patient table 15 and in the functional scope of the medical imaging system.

In particular, in this case, the operative can be requested to adapt the measurement protocol such that all measurement functions are included in the functional scope of the patient table 15 and in the functional scope of the medical imaging system.

Alternatively, the measurement function or the measurement functions that are not included in both functional scopes can automatically be replaced, restricted, or deleted by an equivalent measurement function. A restriction of the measurement function can take place as described below with respect to the travel path.

Alternatively, the measurement protocol can be adapted, in that a new measurement protocol is received. For the newly received measurement protocol, the steps of checking CHECK-2, providing PROV, and, where appropriate, adapting ADA-2 are performed anew.

Alternatively, the measurement protocol formed as described above can be received in a method step of receiving REC-4 as described above. One of the measurement functions, in this case, specifies a measurement travel path. The measurement travel path is the maximum travel path by which the patient table 15 must be moved to perform the examination.

Locking LOCK then includes a method step of checking CHECK-1 whether the measurement travel path is larger than the first and/or the second maximum travel path. If the measurement travel path is larger than one of the two maximum travel paths, locking LOCK also includes a method step of adapting ADA-1 the measurement travel path in the measurement protocol so that the measurement travel path corresponds to the smaller of the first or of the second maximum travel path. In other words, where appropriate, it is ensured that the measurement travel path always corresponds to the smaller of the maximum travel paths.

FIG. 4 shows a compatibility system SYS for producing compatibility of a patient table and of a medical imaging system.

The compatibility system SYS illustrated for producing compatibility of a patient table and of a medical imaging system is designed to execute an inventive method for producing compatibility of a patient table and of a medical imaging system.

The compatibility system SYS can, in particular, be a computer, a microcontroller, or an integrated circuit (IC). Alternatively, the compatibility system SYS can be a real or virtual computer network (a technical term for a real computer network is "cluster," and a technical term for a virtual computer network is "cloud"). The compatibility system SYS can be designed as a virtual system that is executed on a computer, a real computer network, or a virtual computer network (a technical term is "virtualization").

The interface SYS.IF can be a hardware or software interface (for example, a PCI bus, USB, or FireWire). The computing unit SYS.CU can include hardware and/or software elements, for example a microprocessor or a so-called FPGA (Field Programmable Gate Array). The memory unit SYS.MU can be designed as a non-permanently working main memory (Random Access Memory, RAM) or as a permanent mass memory (hard disk, USB stick, SD card, solid state disk (SSD)).

The interface SYS.IF can, in particular, include a plurality of sub-interfaces that execute different method steps of the respective inventive method. In other words, the interface SYS.IF can be designed as a plurality of interfaces SYS.IF. The computing unit SYS.CU can, in particular, include a plurality of sub-computing units that execute different method steps of the respective inventive method. In other words, the computing unit SYS.CU can be designed as a plurality of computing unit SYS.CU.

Figure 5:
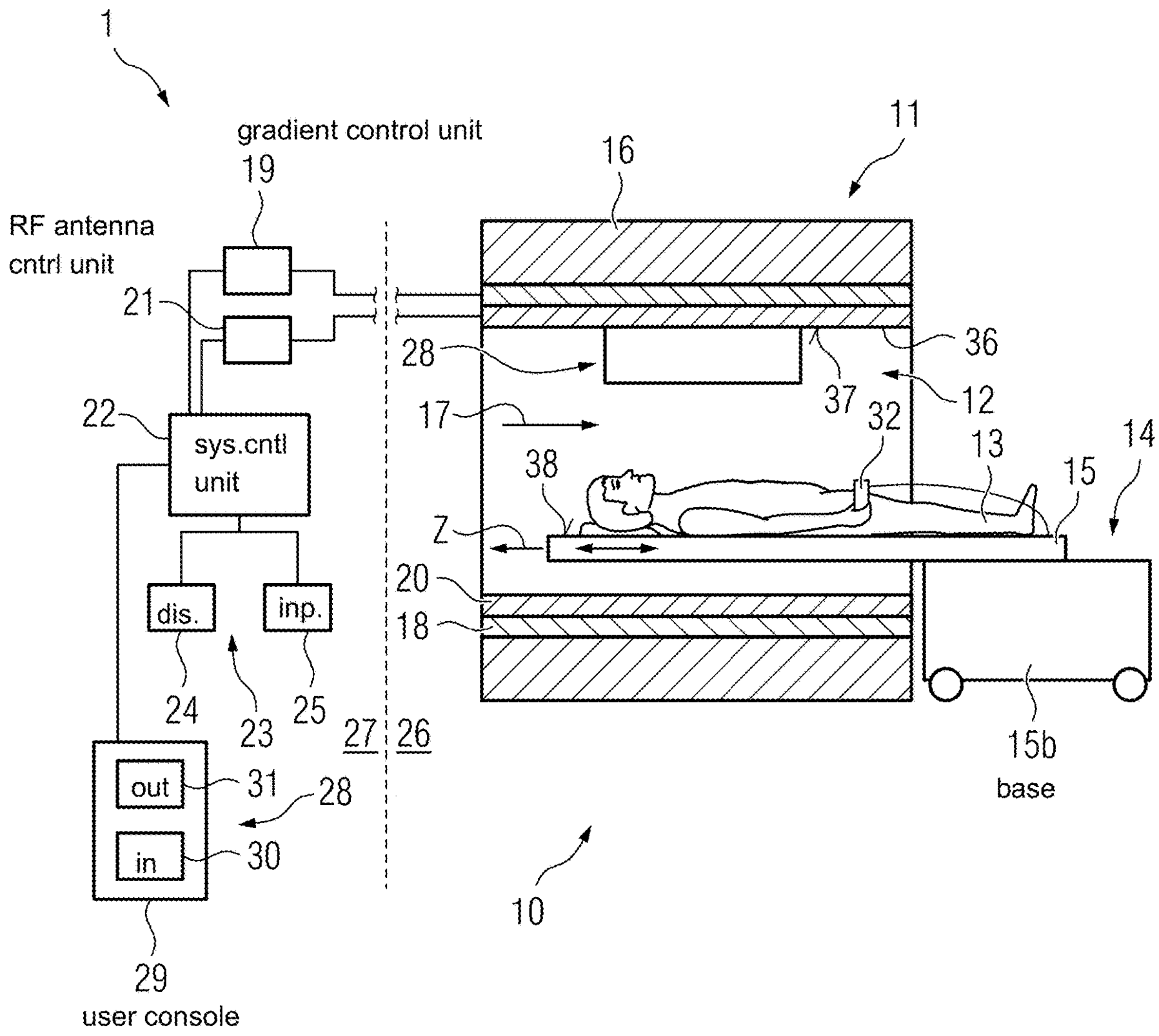
FIG. 5 shows an exemplary aspect of a magnetic resonance tomography system.

FIG. 5 shows an exemplary aspect of a magnetic resonance tomography (acronym: MRT) system 1.

The MRT system 1 is an example of a medical imaging system.

The MRT system 1 includes a magnetic resonance device 10. The magnetic resonance device 10 includes a scanner unit 11 formed by a magnet unit. Furthermore, the magnetic resonance device 10 has a patient receiving area 12 for receiving a patient 13. The patient receiving area 12 in the present exemplary aspect is designed to be cylindrical and is cylindrically surrounded in a circumferential direction by the scanner unit 11, in particular by the magnet unit. However, an aspect of the patient receiving area 12 deviating from this is, in principle, always conceivable. The patient 13 can be pushed and/or moved into the patient receiving area 12 by means of a patient positioning device 14 of the MRT system 1. To this end, the patient positioning device 14 has a patient table 15 that is designed to be able to move inside the patient receiving area 12. In particular, the patient table 15 is here mounted so as to be movable in the direction of a longitudinal extension of the patient receiving area 12 and/or in the z-direction. In this case the patient table 15 is designed to be able to travel or move relative to its base 15*b*. The base 15*b* is designed to support or restrain a reclining area of the patient table 15. In some aspects of the disclosure, the patient table 15 is a mobile patient table. In this case the patient table 15 is designed to be able to travel by means of its base 15*b* by means of a roller system and/or a rail system.

The patient receiving area 12 includes a casing 36 with an inner wall 37 surrounding the patient receiving area 12. The casing 36 surrounding the patient receiving area 12 is, in the present exemplary aspect, designed to be integral with the radio-frequency antenna unit 20, in particular, a side of the radio-frequency antenna unit 20 facing the patient receiving area 12. In an alternative aspect of the disclosure, the casing 36 surrounding the patient receiving area 12 can also form a unit separate from the radio-frequency antenna unit 20.

The scanner unit 11, in particular the magnet unit, includes a superconducting base magnet or body coil 16 for generating a strong and, in particular, constant magnetic field 17. Furthermore, the scanner unit 11, in particular the magnet unit, has a gradient coil unit 18 for generating magnetic field gradients, which are used for position encoding during imaging. The gradient coil unit 18 is controlled by means of a gradient control unit 19 of the MRT system 1. The scanner unit 11, in particular the magnet unit, further includes a radio-frequency antenna unit 20 for excitation of a polarization, which occurs in the constant magnetic field 17 generated by the body coil 16. The radio-frequency antenna unit 20 is controlled by a radio-frequency antenna control unit 21 of the MRT system 1 and beams radio-frequency magnetic resonance sequences into the patient receiving area 12 of the magnetic resonance device 10.

To control the body coil 16, the gradient control unit 19, and the radio-frequency antenna control unit 21, the MRT system 1 has a system control unit 22. The system control unit 22 controls the MRT system 1 centrally, such as, for example, the performance of a predetermined imaging gradient echo sequence. Furthermore, the system control unit 22 includes an evaluation unit, not shown in greater detail, for evaluating medical image data or MRT image data captured during the magnetic resonance examination or examination.

Furthermore, the MRT system 1 includes a user interface 23, which is connected to the system control unit 22. Control information, such as, for example, imaging parameters, as well as reconstructed MRT image data, can be displayed on a display unit 24, for example, on at least one monitor, the user interface 23 for a medical operative or medical personnel. Furthermore, the user interface 23 has an input unit 25, by means of which information and/or parameters can be input by the medical operative during a measurement operation.

In addition, the user interface 23 can be designed to output a warning if a setting of a travel path by the medical operative or by an examination protocol exceeds the specified maximum travel path. In particular, the user interface 23 can be designed to output information if the specified maximum travel path is smaller than the maximum possible travel path.

The scanner unit 11 of the magnetic resonance device 10 is arranged together with the patient positioning device 14 inside an examination room 26. In contrast, the system control unit 22 is arranged together with the user interface 23 inside a control room 27. The control room 27 is designed to be separate from the examination room 26. In particular, the examination room 26 is shielded from the control room 27 with respect to radio-frequency radiation. During an examination, the patient 13 is located inside the examination room 26, whereas, in contrast, the medical operative is generally inside the control room 27.

For communication and/or exchanging information about the patient 13 with the medical operative during an examination, the MRT system 1 has a communication unit 28. On the user side, the communication unit 28 has a communication element designed as a user console 29. The communication element, in particular the user console 28, is preferably arranged inside the control room 27. The user console 29 has an input element 30 and an output element 31. The input element 30 and/or the output element 31 can, in this case, be designed as an acoustic and/or visual input element 30 and/or output element 31.

Furthermore, on the patient side the communication unit 28 has a first communication element, which is designed as an input element 32. By means of the input element 32, the patient 13 can notify the operator, in particular the medical operative, of a condition, for example, any discomfort, during the examination. In the present exemplary aspect, the input element 32 is designed as a patient call ball or alarm ball. However, in principle, further input elements 32, such as a microphone, which appears useful to the person skilled in the art, are also possible in a further aspect of the communication unit 28.

The MRT system 1 illustrated can, of course, include further components that MRT system 1 usually contains. The general functionality of an MRT system 1 is furthermore known to the person skilled in the art so that a detailed description of the further components is dispensed with.

Where not yet explicitly done but where useful and within the meaning of the disclosure, individual exemplary aspects, individual partial aspects, or features thereof can be combined or exchanged without departing from the scope of the present disclosure. Advantages of the disclosure described with reference to an exemplary aspect also apply to other exemplary aspects without being explicitly mentioned, where transferable.

The invention claimed is:

1. A computer-implemented method for producing compatibility of a patient table and a medical imaging system, wherein the patient table is designed to position a patient during an examination with the medical imaging system, the method comprising:

receiving a functional scope of the patient table including at least one function;

receiving a functional scope of the medical imaging system including at least one function;

comparing the functional scope of the patient table with the functional scope of the medical imaging system; and in response to the at least one function not being included in the functional scope of the patient table and in the functional scope of the medical imaging system, locking the at least one function by automatically adjusting a functionality of at least one component of the patient table or the medical imaging system that is associated with the at least one function from a predetermined functional operation to a reduced functional operation for use during the examination, to thereby prevent equipment malfunction during the examination with the medical imaging system, wherein the predetermined functional operation comprises indicating a first number of plugin locations for local coils, wherein the reduced functional operation comprises deactivating one or more of the first number of plugin locations to provide a second number of plugin locations that is less than the first number of plugin locations, and wherein the deactivating the one or more of the first number of plugin locations prevents data from being received from or sent to local coils that have been plugged into the one or more of the first number of plugin locations.

2. The method as claimed in claim 1, wherein the patient table is a mobile patient table.

3. The method as claimed in claim 1, wherein the medical imaging system is a magnetic resonance tomography system.

4. The method as claimed in claim 1, wherein the at least one function included in the functional scope of the patient table and/or of the medical imaging system relates to:
travel path, number of plugin locations for local coils, transmission path for a local coil, support for local shim coils, maximum supported patient weight, connection for a vacuum cushion, connection for a patient communication system, or interfaces to other systems.

5. The method as claimed in claim 1, wherein:
the functional scope of the patient table includes a function that indicates a first number of plugin locations for local coils,
the functional scope of the medical imaging system includes a function that indicates a second number of plugin locations for local coils,
the first number is larger than the second number, and
the locking the at least one function comprises locking the plugin locations on the patient table, which are not indicated by the function included in the functional scope of the medical imaging system.

6. The method as claimed in claim 1, wherein:
the functional scope of the patient table includes a function that indicates a first maximum travel path of the patient table,
the functional scope of the medical imaging system includes a function that indicates a second maximum travel path of the patient table,
the first maximum travel path is larger than the second maximum travel path, and
the locking the at least one function comprises restricting an actuation of the patient table such that the patient table is movable only along the second maximum travel path.

7. The method as claimed in claim 1, wherein:
the functional scope of the patient table includes a function that indicates a first maximum travel path of the patient table,
the functional scope of the medical imaging system includes a function that indicates a second maximum travel path of the patient table,
the first maximum travel path is not equal to the second maximum travel path, and
further comprising:
receiving a measurement protocol that specifies a measurement travel path required for performance of the examination with the medical imaging system, wherein the locking the at least one function comprises:
checking whether the measurement travel path is larger than the first and/or the second travel path, and
if the measurement travel path is larger than the first and/or the second maximum travel path, adapting the measurement travel path in the measurement protocol so that the measurement travel path corresponds with the smaller of the first and of the second maximum travel path.

8. The method as claimed in claim 1, further comprising:
receiving a measurement protocol,
wherein the measurement protocol includes measurement functions required for performance of the examination with the medical imaging system, and
wherein the locking the at least one function comprises:
checking whether at least one of the measurement functions is not included in the functional scope of the patient table and/or the functional scope of the medical imaging system, and
providing information about which of the measurement functions is not included in the functional scope of the patient table and/or in the functional scope of the medical imaging system.

9. The method as claimed in claim 8, wherein the locking the at least one function further comprises:
adapting the measurement protocol such that the measurement functions are adapted so that all measurement functions are included in the functional scope of the patient table and in the functional scope of the medical imaging system.

10. A system for producing compatibility of a patient table and a medical imaging system, wherein the patient table is designed to position a patient during an examination with the medical imaging system, the system comprising:
an interface configured to:
receive a functional scope of the patient table, wherein the functional scope of the patient table includes at least one function; and
receive a functional scope of the medical imaging system, wherein the functional scope of the medical imaging system includes at least one function; and
processing circuitry configured to:
compare the functional scope of the patient table with the functional scope of the medical imaging system; and
in response to the at least one function not being included in the functional scope of the patient table and in the functional scope of the medical imaging system, locking the at least one function by automatically adjusting a functionality of at least one component of the patient table or the medical imaging system that is associated with the at least one function from a predetermined functional operation to a reduced functional operation for use during the examination, to thereby prevent equipment malfunction during the examination with the medical imaging system,
wherein the predetermined functional operation comprises indicating a first number of plugin locations for local coils,
wherein the reduced functional operation comprises deactivating one or more of the first number of plugin locations to provide a second number of plugin locations that is less than the first number of plugin locations, and
wherein the deactivating the one or more of the first number of plugin locations prevents data from being received from or sent to local coils that have been plugged into the one or more of the first number of plugin locations.

11. A non-transitory computer-readable storage medium configured to store program instructions that, when executed by a system for producing compatibility of a patient table and a medical imaging system, wherein the patient table is designed to position a patient during an examination with the medical imaging system, cause the system to:
receive a functional scope of the patient table, wherein the functional scope of the patient table includes at least one function; and
receive a functional scope of the medical imaging system, wherein the functional scope of the medical imaging system includes at least one function; and
compare the functional scope of the patient table with the functional scope of the medical imaging system; and
in response to the at least one function not being included in the functional scope of the patient table and in the functional scope of the medical imaging system, locking the at least one function by automatically adjusting a functionality of at least one component of the patient table or the medical imaging system that is associated with the at least one function from a predetermined functional operation to a reduced functional operation for use during the examination, to thereby prevent equipment malfunction during the examination with the medical imaging system, wherein the predetermined functional operation comprises indicating a first number of plugin locations for local coils, wherein the reduced functional operation comprises deactivating one or more of the first number of plugin locations to provide a second number of plugin locations that is less than the first number of plugin locations, and wherein the deactivating the one or more of the first number of plugin locations prevents data from being received from or sent to local coils that have been plugged into the one or more of the first number of plugin locations.

12. The method as claimed in claim 1, further comprising:

in response to (i) the at least one function being included in the functional scope of the patient table and in the functional scope of the medical imaging system, and (ii) a functional characteristic of the at least one function included in the functional scope of the patient table being different than a functional characteristic of the at least one function included in the functional scope of the medical imaging system, locking the at least one function.

13. The method as claimed in claim 1, wherein the predetermined functional operation comprises a first range of movement of the patient table along a travel path, and wherein the reduced functional operation comprises a restriction of actuation of the patient table to a second range of movement that is less than the first range of movement.

14. The method as claimed in claim 1, wherein the comparing the functional scope of the patient table with the functional scope of the medical imaging system comprises determining compatibility between the first number of plugin locations on the patient table and readable plugin location positions supported by the medical imaging system.

* * * * *